US009271858B2

(12) United States Patent
Ben-Meir et al.

(10) Patent No.: US 9,271,858 B2
(45) Date of Patent: Mar. 1, 2016

(54) VARIABLE MODULUS BODY BRACE AND BODY BRACE SYSTEM

(71) Applicant: SoftArmour LLC, Rye, NY (US)

(72) Inventors: David Amos Ben-Meir, Rye, NY (US); Allan Sanford, Wurtsboro, NY (US); Christen Egan, Fairfield, NJ (US); Gibran Esquenazi, Cypress, TX (US); Richard Hutchison, Troy, NY (US); Nathaniel Mowell, Saratoga Springs, NY (US); Russell Scott Miller, Rexford, NY (US)

(73) Assignee: SOFTARMOUR LLC, Rye, NY (US)

( * ) Notice: Subject to any disclaimer, the term of this patent is extended or adjusted under 35 U.S.C. 154(b) by 134 days.

(21) Appl. No.: 14/250,163

(22) Filed: Apr. 10, 2014

(65) Prior Publication Data

US 2015/0018733 A1     Jan. 15, 2015

Related U.S. Application Data

(60) Provisional application No. 61/957,844, filed on Jul. 15, 2013.

(51) Int. Cl.
*A61F 5/00*     (2006.01)
*A61F 5/01*     (2006.01)
*A61F 5/058*    (2006.01)

(52) U.S. Cl.
CPC ............ *A61F 5/0104* (2013.01); *A61F 5/0109* (2013.01); *A61F 5/058* (2013.01);
(Continued)

(58) Field of Classification Search
CPC ............... A61F 2005/0155; A61F 2005/0167; A61F 2005/0188; A61F 2210/0066; A61F 2210/0076; A61F 2250/0012; A61F 5/0104; A61F 5/0109; A61F 5/058; A61F 5/0585; A61F 5/01; A61N 1/325; A61N 1/0428; A61N 1/0436; A61N 1/044; A61N 1/0448; A61N 1/0492; A61N 1/205; A61N 1/30; A61N 1/303; A61N 1/306; C04B 35/624; G02B 2006/12145
USPC ................ 602/2, 5–6, 16, 19, 20–28, 60–63; 128/882; 5/624; 66/202
See application file for complete search history.

(56) References Cited

U.S. PATENT DOCUMENTS 4,286,586 A * 9/1981 Potts ...................... A61F 13/04
427/2.1
4,923,057 A 5/1990 Carlson et al.
(Continued)

FOREIGN PATENT DOCUMENTS

WO    WO 2004/079832 A2    9/2004

OTHER PUBLICATIONS

CheckLight, Reebok website, available at http://shop.reebok.com/us/content/CheckLight, Mar. 28, 2014.
(Continued)

*Primary Examiner* — Michael Brown
(74) *Attorney, Agent, or Firm* — Gordon & Jacobson, P.C.

(57) ABSTRACT

A brace for a part of a body includes a first conductive fiber associated with a first polarity, and a second conductive fiber associated with a second polarity different from the first polarity. The second fiber is woven together with the first fiber and insulated from the first fiber. The brace also includes a selectively electrically activated cross-linking agent between the first and second fibers. The agent is constructed to cross-link in a first active mode when the first and second fibers are electrified and is constructed to not cross-link in a second inactive mode when the first and second fibers are not electrified. The brace surrounds a body part, such as a knee or neck. The agent can include an ER fluid and/or EAP. A brace system includes a selectively electrically activated brace for the part of the body.

11 Claims, 9 Drawing Sheets

(52) U.S. Cl.
CPC ...... *A61F 5/0585* (2013.01); *A61F 2005/0155* (2013.01); *A61F 2005/0167* (2013.01); *A61F 2005/0188* (2013.01); *A61F 2210/0066* (2013.01); *A61F 2210/0076* (2013.01); *A61F 2250/0012* (2013.01)

(56) References Cited

U.S. PATENT DOCUMENTS

| | | | |
|---|---|---|---|
| 6,969,365 B2 * | 11/2005 | Scorvo | A61F 5/0125 601/33 |
| 7,279,009 B2 | 10/2007 | Herr et al. | |
| 8,258,238 B2 | 9/2012 | Boersma | |
| 2006/0264795 A1 * | 11/2006 | Christensen | A61F 5/0111 602/27 |
| 2007/0060862 A1 * | 3/2007 | Sun | A61K 8/19 604/20 |
| 2012/0189795 A1 | 7/2012 | Wong | |
| 2013/0319859 A1 | 12/2013 | Wong | |

OTHER PUBLICATIONS

"Smart Fluids Move into the Marketplace", Jennifer Ouellette, The Industrial Physicist, American Institute of Physics, Dec. 2003/Jan. 2004, pp. 14-17.

* cited by examiner

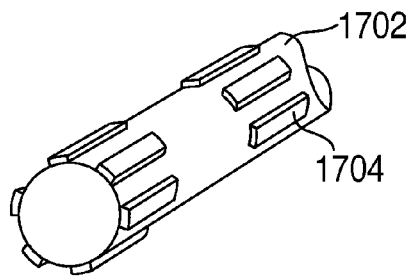
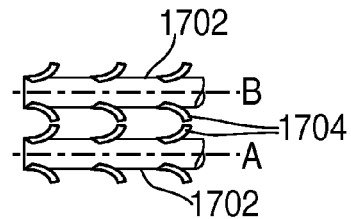
FIG. 17　　　　　FIG. 19
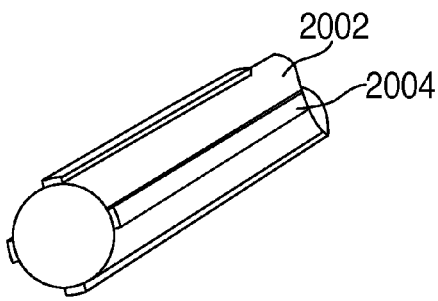
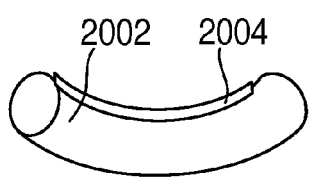
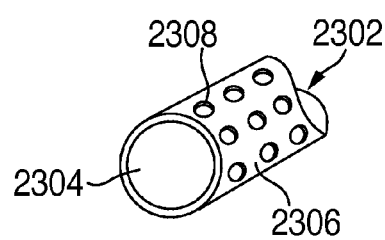
FIG. 20　　FIG. 21　　FIG. 22
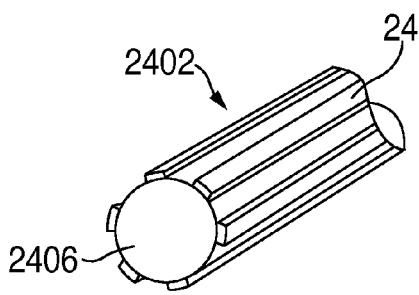
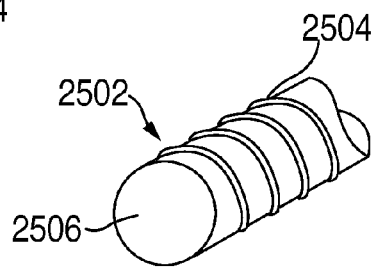
FIG. 24　　FIG. 25
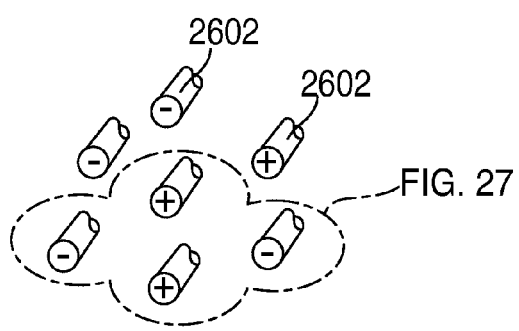
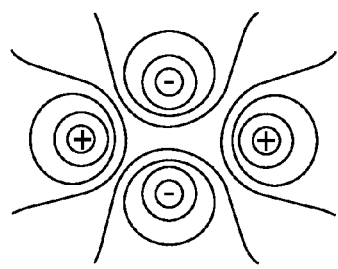
FIG. 26　　FIG. 27

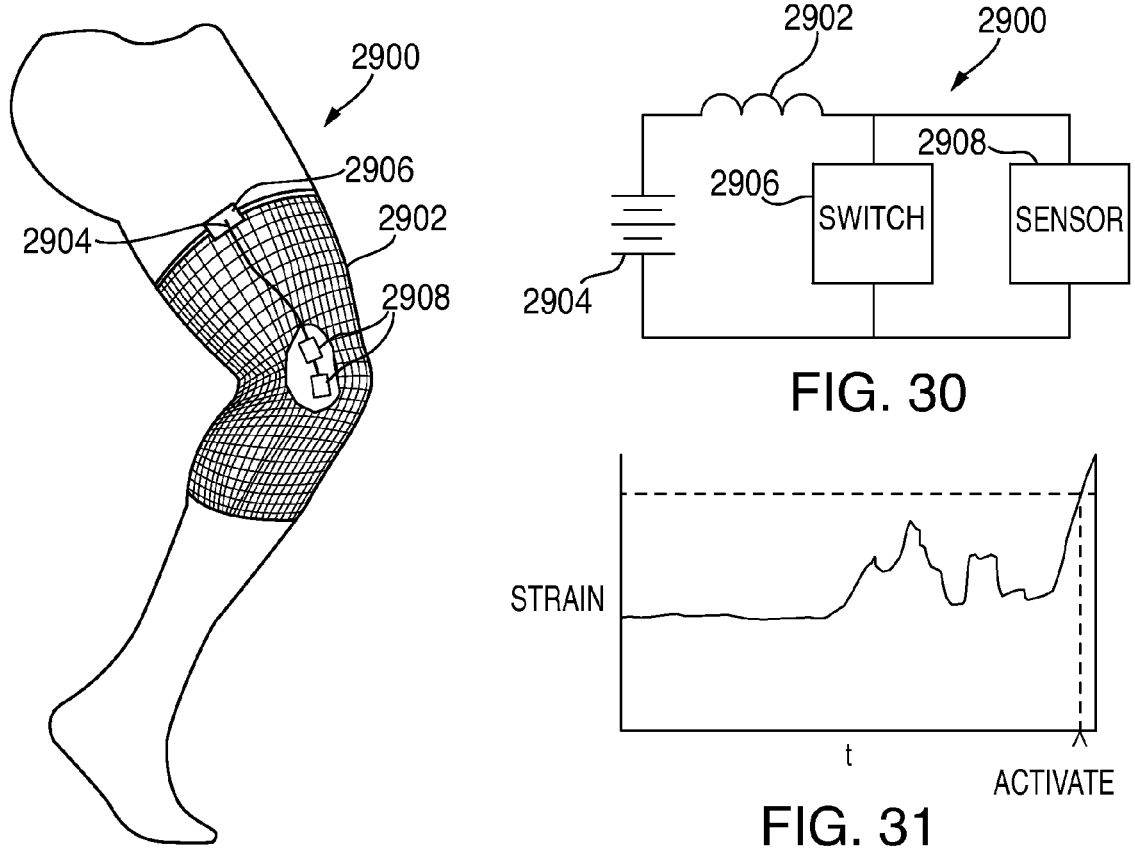
FIG. 29
FIG. 30
FIG. 31
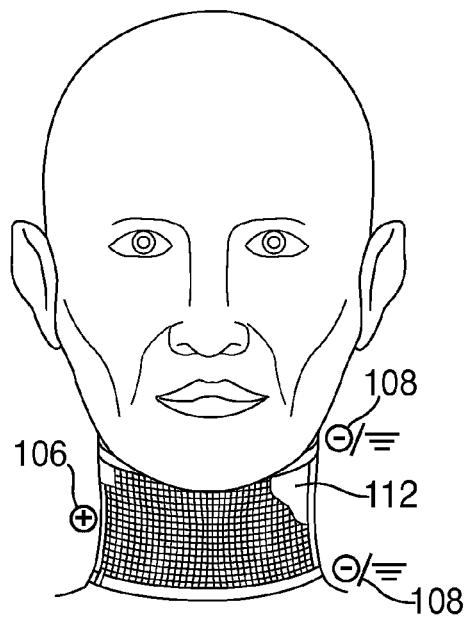
FIG. 32

VARIABLE MODULUS BODY BRACE AND BODY BRACE SYSTEM

CROSS-REFERENCE TO RELATED APPLICATIONS

This application claims priority under 35 U.S.C. §119 to U.S. Provisional Patent Application No. 61/957,844 filed Jul. 15, 2013, the entire content of which is incorporated herein by reference.

BACKGROUND

1. Field

The following disclosure relates to load distribution to an object and, more specifically, an apparatus and system for a variable modulus body brace.

2. State of the Art

Various types of body braces are known. For example, knee, back, arm, and ankle braces are common. Typical flexible braces are formed of a fabric material that is wrapped around a portion of the body in an attempt to reinforce that portion. Typical rigid braces are formed of composite (or fabric) structure that wraps around a portion of the body with metal supports that are mechanically secured (or supported by) to the composite (or fabric) structure. The metal supports are provided to reinforce a part of the body.

SUMMARY

In a first aspect, a brace for at least a part of the body includes a first conductive fiber associated with a first polarity, and a second conductive fiber associated with a second polarity different from the first polarity. The second fiber is woven together with the first fiber and insulated from the first fiber. The brace also includes a selectively electrically activated cross-linking agent between the first and second fibers. The agent is constructed to cross-link in a first active mode when the first and second fibers are electrified and is constructed to not cross-link in a second inactive mode when the first and second fibers are not electrified. The non-cross-linked state of the agent can allow the first and second fibers to move relative to one another in a flexible and compliant manner, which can accommodate movement of the body part. The cross-linked state of the agent can act to bind and/or limit relative movement of the first and second fiber, which can limit the movement of the body part and protect the body part from injury.

The cross-linked state and the non-cross-linked state can alternate while the brace is worn on the body part based, for example, on a monitored threat of injury to the part of the body. For example, in the case of a knee brace worn while playing football, the cross-linked state can be triggered to occur during periods of time when a sensor senses deflections of the knee or forces on the knee that are associated with deflections or forces that can precede injury to the knee. After the threat of injury subsides and during periods of time when such a sensor does not sense deflections or forces that may precede injury to the knee, the non-cross linked state can be triggered to occur. Thus, it will be appreciated that while the brace is worn on the body transitions of the states between cross-linked and non-cross-linked may occur repeatedly.

In one embodiment, the cross-linking agent is an ER fluid. In another embodiment, the cross-linking agent is EAP. The modulus of elasticity of the brace can be varied by selectively activating or deactivating the cross-linking agent, such as by selectively electrifying the first and second fibers.

In at least one embodiment, the brace is generally annular and configured to surround a body part. In one example embodiment, the brace has suitable dimensions and is constructed to surround the knee and surrounding portions of the leg. In another example embodiment, the brace has suitable dimensions and is constructed to surround the neck.

In at least one embodiment, the agent is activated based at least on a measurement of a sensor, such as an accelerometer, positioned at least on the brace.

In one embodiment, the brace includes a first terminal of the first polarity electrically connected to the first conductive fiber and a second terminal of the second polarity electrically connected to the second conductive fibers, and the first and second terminals are electrically isolated from each other. In one embodiment, at least one of the first conductive fiber and the second conductive fiber includes electrical insulation. Also, in one embodiment, the first plurality of fibers and the second plurality of fibers are arranged in a warp/weft pattern in which the first fiber forms the warp and the second fiber forms the weft.

In one embodiment, the first terminal and the second terminal are spaced longitudinally from each other and the first conductive fiber extends longitudinally from the first terminal towards the second terminal, but is spaced therefrom. Also, the second conductive fiber extends longitudinally from the second terminal towards the first terminal, but is spaced therefrom, and the first conductive fiber is intertwined with the second conductive fiber longitudinally.

In a second aspect, a brace for at least a part of a body includes a first conductive strip comprised of a first plurality of conductors and a first selectively electrically activated agent between the first plurality of conductors. The first agent is constructed to alter the modulus of the first strip in an active mode when the first plurality of conductors are electrified and is constructed to not alter the modulus of the first strip in an inactive mode when the first plurality of conductors are not electrified. The brace also includes a second conductive strip comprised of a second plurality of conductors and a second selectively electrically activated agent between the second plurality of conductors. The second agent is constructed to alter the modulus of the second strip in an active mode when the second plurality of conductors are electrified and is constructed to not alter the modulus of the second strip in an inactive mode when the second plurality of conductors are not electrified. The first strip is woven together with the second strip, and the first and second strips are electrically insulated from each other. The first and second agents can include an ER fluid and/or EAP.

In a third aspect, a brace system for protecting at least a part of the body includes a selectively electrically activated brace for the part of the body. The brace is constructed to have a first modulus of elasticity in an inactivated state and to have a second modulus, larger than the first modulus, in an activated state. The system also includes a sensor electrically connected to the brace. The sensor is constructed to sense the condition of the brace and to determine whether or not to activate the brace based on the sensed condition. The system further includes a power source electrically connected to the sensor and constructed to selectively power the brace. Also, the system includes a switch electrically connected to the brace and the power source. The switch is constructed to selectively connect the power source to the brace in the activated state and to disconnect the power source from the brace in the inactivated state.

In one embodiment, the brace includes a first conductive fiber, a second conductive fiber, and a selectively electrically activated agent between the first and second fiber. The agent is constructed to alter the modulus in a first active mode when the first and second fibers are electrified and is constructed to not alter the modulus a second inactive mode when the first and second fibers are not electrified. The agent can include an ER fluid or an EAP.

A more complete understanding will become apparent to those skilled in the art upon reference to the detailed description taken in conjunction with the provided figures.

BRIEF DESCRIPTION OF THE DRAWINGS

FIG. 17 is a perspective view of an embodiment of a conductive fiber in accordance with an aspect of the application.

FIG. 19 is a side elevation view of portions of two of the conductive fibers of FIG. 17 shown in an activated condition.

FIG. 20 is a perspective view of an embodiment of a conductive fiber in accordance with an aspect of the application.

FIG. 21 is a perspective view of the conductive fibers shown in FIG. 20 shown in an activated condition.

FIG. 22 is a perspective view of an embodiment of a conductive fiber in accordance with an aspect of the application.

FIG. 24 is a perspective view of an embodiment of a conductive fiber in accordance with an aspect of the application.

FIG. 25 is a perspective view of an embodiment of a conductive fiber in accordance with an aspect of the application.

FIG. 26 is a schematic view of a plurality of conductive fibers.

FIG. 27 is a view of a quadrupole electric field arrangement associated with four conductive fibers in FIG. 26.

FIG. 29 shows a view of a knee brace system in accordance with an aspect of the application.

FIG. 30 is a wiring diagram of the knee brace system of FIG. 29.

FIG. 31 is a graph showing a relationship between strain and time for the knee brace system of FIG. 30.

FIG. 32 shows a front elevation view of the brace shown in FIG. 1 worn on a neck in accordance with an aspect of the application.

DETAILED DESCRIPTION

Figure 1:
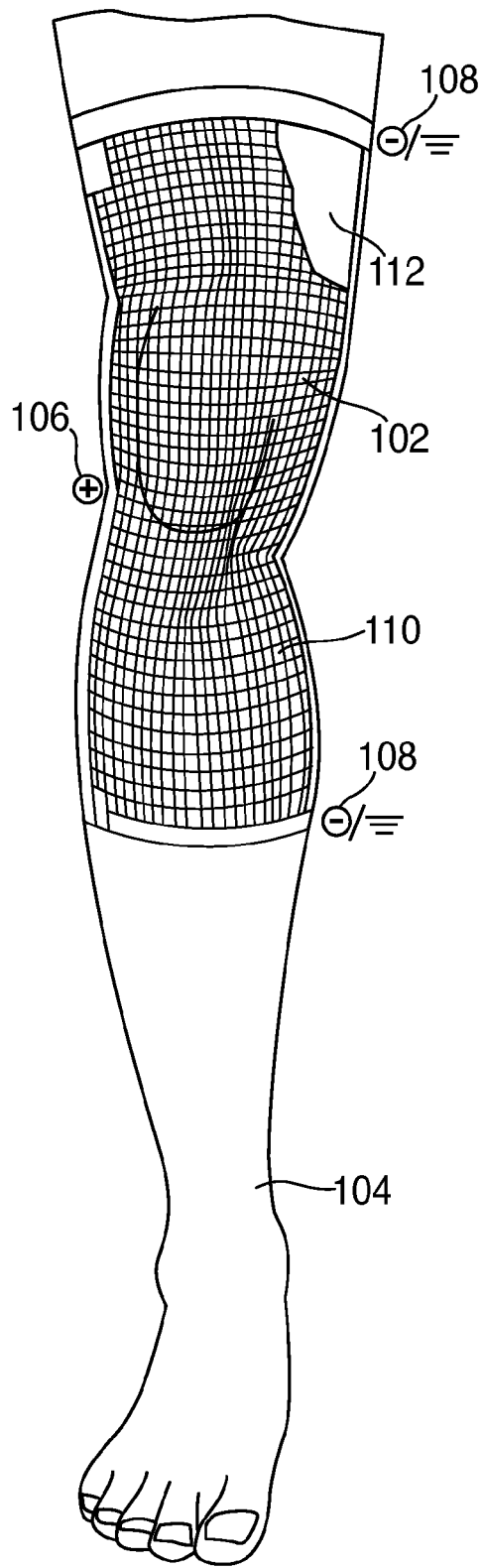
FIG. 1 shows a front elevation view of a knee brace worn on a leg in accordance with an aspect of the invention.

Typical sports injuries include torn ligaments and concussions. For example, during a football scrimmage, a side impact of a leg that is planted can result in excessive valgus extension, stressing both the medial collateral ligament (MCL) and anterior cruciate ligament (ACL). Maximum MCL strain is between 6 and 10 percent and occurs at a valgus displacement angle of about 7 degrees (beyond normal). Conventional knee braces (straps to thigh and calf, with a stiff hinged structure between) reduce stress on the ACL in twisting and provide some protection against valgus deflection. However, such conventional braces are rarely used prophylactically, because they are cumbersome and because the hinged side braces do not provide large moment of inertia to resist valgus bending. Moreover, such conventional braces distribute concentrated loads further up the femur and down the tibia reducing the overall bending moment at the knee and the resulting stresses on the ligaments.

Also, concussion injuries are directly related to the acceleration experienced by the head relative to the neck and the rest of the body. Field studies with helmets have been used to assess these values. Accelerations of 70-g are sufficient to cause concussion if applied for 15 milliseconds.

Moreover, neck injuries can occur when a rider of a bicycle or motorcycle are thrown forward from the vehicle they are riding from and land head-first on the ground. In such a case, when the head hits the ground first the rest of the rider's body is moving forward due to momentum and bends with respect to the head about the neck. Severe deflections of the neck can cause permanent neck injury and paralysis.

Ligament and concussive sports injuries as well as neck injuries are distinguishable from other sports injuries, such as pole impacts (in skiing) and projectile impacts (e.g., from hockey pucks), by the time scale during which the injuries occur. Many ligament and concussive injuries occur on a time scale of several to several tens of milliseconds, while projectile sports injuries occur on a sub-millisecond time scale. While passive body armor utilizing shear thickening fluid can be used in these fast time response regimes, body armor or bracing for slower time response regimes are not available to athletes to help limit sports injuries. The following disclosure describes various embodiments of braces and systems that address the deficiencies of braces for such slower time response regimes.

The following discussion mentions various types of materials, such as electrorheological (ER) fluid and electroactive polymer (EAP). ER fluid is a suspension of fine (on the order of tens of nanometers) non-conducting particles in an electrically insulating fluid. ER fluids are "Bingham" fluids. When initially subject to an electric field, the ER fluid does not flow at until a static threshold shear stress limit is reached in the fluid. Once the static shear stress limit is reached in the ER fluid, the ER fluid flows and the shear stress needed for flow increases as the shear rate increases. Thus, once the static threshold is reached, the viscosity of the ER fluid increases as the shear stress increases. Electroactive polymer (EAP) is a polymeric material that exhibits a change in size or shape when in the presence of an electric field.

FIG. 1 shows a cylindrical knee brace 102 worn on a leg 104. The brace 102 includes a positive terminal 106 and a negative terminal 108 and insulated mesh 110 of fiber woven in a conventional warp/weft pattern between the positive and negative terminals 106, 108. In one embodiment, only one negative terminal 108 is employed at one end of the brace 102. The negative terminal 108 may also be a ground terminal. The positive terminal 106 is insulated from the negative terminal 108. The terminals 106, 108 can be flexible. For example, in one embodiment, the terminals are formed of at least one of woven metal wire and woven metal-coated polymer.

Figure 2:
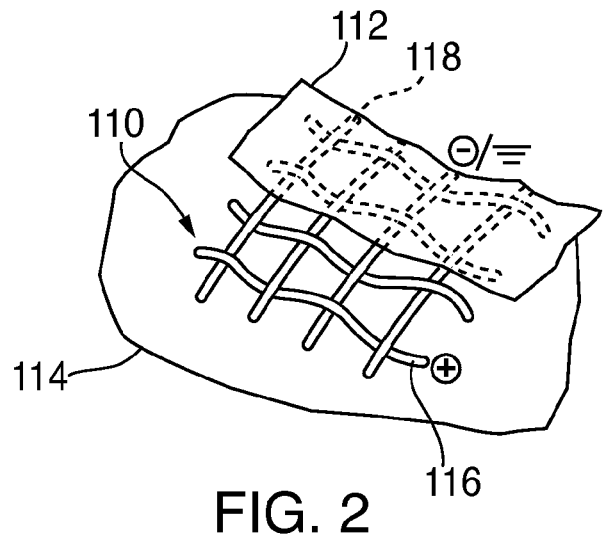
FIG. 2 shows a partial cutaway assembly view of a woven conductive fiber mesh of the knee brace of FIG. 1

As shown in FIG. 2, the mesh includes conductive fibers 116 of the warp and conductive fibers 118 of the weft, which are of different polarities. In one embodiment, the warp conductive fibers 116 are electrically connected to the positive terminal 106 and the weft conductive fibers 118 are electrically connected to the negative terminal 108. The positive and negative terminals 106, 108 function as electric busses to electrically connect all of the conductive fibers 116, 118 of a respective polarity together. The brace 102 also includes an outer cylindrical sheath 112 (FIGS. 1 and 2) and an inner cylindrical sheath (FIG. 2) that define an annular space in which the mesh 110 is disposed.

The material composition and the conductivity of conductive fibers 116, 118 can vary. For example, the conductive fibers 116, 118 can be formed of at least one of conductive polymer, fine metal wire, metalized polymer filament, and graphene. Graphene is a non-isotropic conductor material that has high electrical conductivity and high tensile strength. The conductive fibers 116, 118 can also be formed of hollow tubes filled with a conductive material, which may be a liquid or solid.

Figure 3:
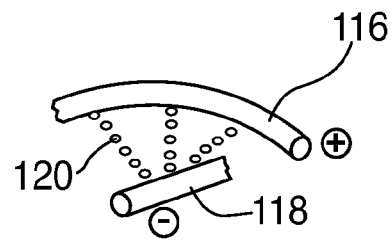
FIG. 3 shows an exploded view of a portion of the mesh shown in FIG. 2, along with a schematic representation of electrorheological (ER) fluid.

In one embodiment, shown in FIG. 3, an ER fluid 120 is disposed between the conductive fibers 116, 118 and is retained between the annular space between the inner sheath 114 and the outer sheath 112. As noted above, the viscosity of ER fluid changes reversibly in response to an electric field. For example, in an activated state, when voltage is applied to the positive and negative conductive fibers 116, 118 of the mesh 110 shown in FIG. 2, the conductive fibers 116, 118 establish an electric field such that the viscosity of the ER fluid 120 increases and effectively links the crossed fibers 116, 118 together so that the modulus of the entire mesh 110 increases and becomes much more rigid than in an inactivated state, when a voltage is not applied.

The ER fluid 120 includes small particles that, when activated by an electric field, align with the electric field and keep the adjacent fibers 116, 118 from moving. In the inactivated state, the ER fluid 120 cannot sustain shear forces, and tensile stresses in individual conductive fibers 116, 118 cannot be transmitted to the adjacent conductive fibers 116, 118; thus the fibers 116 and 118, and the ER fluid are compliant. In the activated or cross-linked state of the ER fluid, the ER fluid 120 exhibits a relatively large increase in viscosity that can act to bind and/or limit relative movement of the conductive fibers 116, 118. In this manner, the ER fluid 120 and the conductive fibers 116, 118 can experience a bulk increase in modulus of elasticity in comparison to the modulus in the inactivated state.

A typical electric field strength requirement for ER fluids is several kV/mm (e.g., about 1 to 5 kV/mm) so that sub-millimeter conductive fiber spacing (e.g., about 10 to 200 microns) is preferred so that the operating voltage (e.g., about 50 to 500 volts) is relatively low. In addition to achieving higher field strength at lower operating voltage, closer conductive fiber spacing also permits ER fluid response time to be relatively lower than for larger conductive fiber spacing.

In addition, the gradient in tensile fiber stress in a homogeneous beam is constant. In the case of a non-homogeneous beam, differential tensile stress (and elongation) will be lower for closer fiber spacing than for larger fiber spacing. The difference in tensile stress is transmitted by shear stress on the ER fluid. Since the ER fluid's ability to sustain shear stress is proportional to field strength, a higher field strength would produce a higher bulk modulus. Moreover, as noted above, the ER fluid has a static shear stress limit, so that the closer the fibers are together, the lower the shear stress between the fibers, and the ER fluid will be able to operate to a higher bulk load limit. Thus, spacing the fibers more closely together increases the modulus of the brace in comparison to spacing the fibers farther apart.

Figure 4:
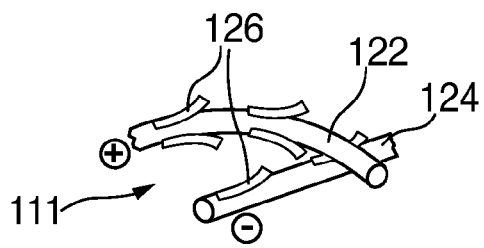
FIG. 4 shows an exploded view of a portion of the mesh shown in FIG. 2, where conductive fibers are formed with an electroactive polymer (EAP).

FIG. 4 shows an alternate embodiment of a mesh 111 that includes conductive fibers 122, 124 that cross. Instead of ER fluid 120 between fibers 122, 124, the fibers 122, 124 shown in FIG. 4 include electroactive polymer (EAP) strips 126. As noted above, the EAP are polymeric materials that exhibit a change in size or shape when in the presence of an electric field. When voltage is applied to the positive and negative conductive fibers 122, 124 of the mesh 111 shown in FIG. 2, the conductive fibers 122, 124 establish an electric field such that the EAP strips 126 become activated. When the EAP strips 126 are activated or cross-linked, the EAP strips 126 curl away from the conductive fibers 122, 124 and physically intertwine and link with other EAP strips 126 on crossing conductive fibers 122, 124. In this manner, the EAP strips 126 and the conductive fibers 116, 118 can experience a bulk increase in modulus of elasticity in comparison to the modulus in the inactivated state, thereby increasing the modulus of elasticity of the entire mesh 111.

In another embodiment (not shown), the arrangement of fibers 122 and 124 shown in FIG. 4 is used in conjunction with ER fluid 120, which can surround the fibers 122 and 124 in a similar matter to that shown in FIG. 3. EAP crosslinking can be enhanced in the presence of ER fluid.

While shown on a leg 104, it should be noted that in another embodiment, the brace 102 can be modified to fit around other parts of the body, including, by way of example and not limitation, the neck, an ankle, the back, and elbow, or other parts of the body by modifications to the size and/or shape of the brace. For example, FIG. 32 shows the brace 102 of FIG. 1 sized to fit around the neck.

Figure 5:
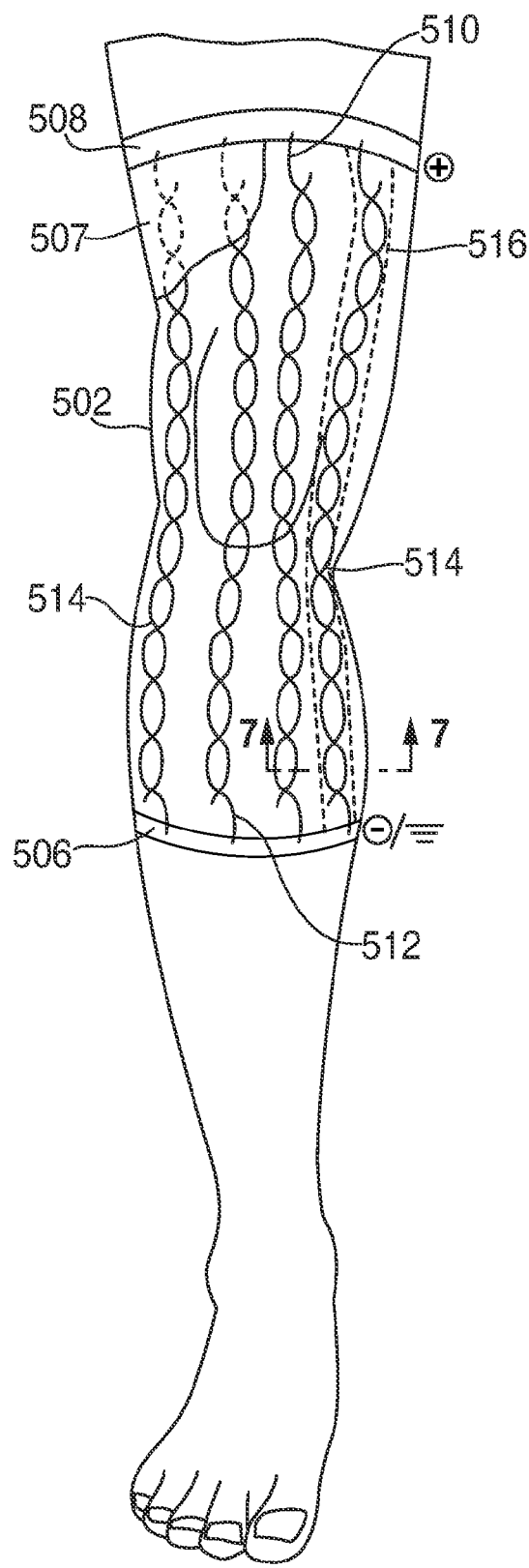
FIG. 5 is an elevation view showing a knee brace worn on a leg in accordance with an aspect of the application.
Figure 6:
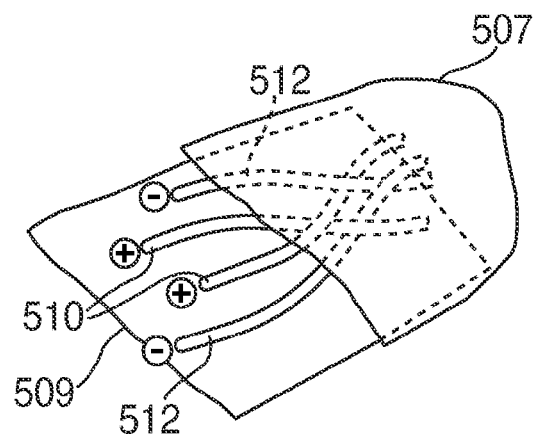
FIG. 6 shows a partial cutaway view of woven conductive fiber fibers of the knee brace of FIG. 5.
Figure 7:
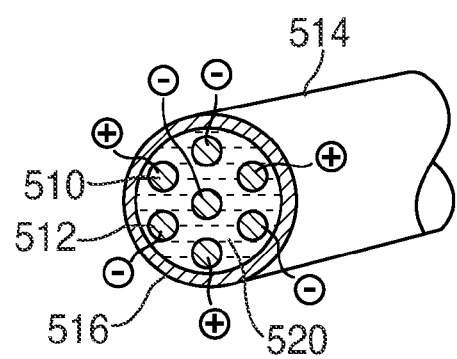
FIG. 7 shows a view of an alternate arrangement of a bundle of woven conductive fibers contained within a sheath along section 7-7 shown in FIG. 5.

FIG. 5 shows another embodiment of a knee brace 502. The knee brace 502 includes opposite polarity terminals 506, 508 at opposite ends of the brace 502 spaced longitudinally apart between a twisted/interlaced weave of insulated conductive fibers 510, 512. The twisted fibers are arranged analogously to "twisted pairs" commonly referred to with respect to telecommunications wiring. A plurality of positive/negative conductive fiber bundles 514 extend longitudinally between the terminals 506, 508. However, positive conductive fibers 510 of each bundle 514 do not extend all the way to the negative terminal 506 and negative conductive fibers 512 of each bundle 514 do not extend all the way to the positive terminal 508. Instead, positive conductive fibers 510 are spaced from the negative terminal 506 and negative conductive fibers 512 are spaced from the positive terminal 508 to avoid shorting. Because the conductive fibers 510, 512 are in close contact for much of their length, the number of crosslinks can be larger in comparison to the same length of fiber in the woven mesh arrangement shown in FIGS. 1 to 4. Although FIG. 5 shows that each bundle 514 includes one positive fiber 510 and one negative fiber 512, it will be understood that each bundle 514 can include a plurality of positive fibers 510 and negative fibers 512, as is shown in FIGS. 6 and 7. For example, continuing with the analogy to "twisted pairs" mentioned above, the bundle 514 can be arranged to include multiple "twisted pairs". The brace 502 includes an outer cylindrical sheath 507 and an inner cylindrical sheath 509, which define an annular space in which the fibers 510, 512 are disposed. The range of diameters of fibers 510, 512 can be between sub-micron to 100 microns. In one embodiment, the fibers 510, 512 are formed of copper and have a diameter of about 20 microns. In one embodiment, the fibers 510, 512 are formed of conductive electrospun insulation fibers, which have diameters that are fractional micron. In one embodiment, the fibers 510, 512 are formed of nylon fibers, which have diameters of about 5 micron to 100 micron. In yet another embodiment, the fibers 510, 512 are formed from very fine fabric threads having diameters of about 10 microns (e.g., 1 denier polyester).

FIGS. 5 and 7 show a bundle 514 of conductive fibers 510, 512 is encased by a flexible sheath 516 that retains an ER fluid 520 between the sheath 516 and the conductive fibers 510, 512. In an activated state, when the fibers 510, 512 are energized the fibers 510, 512 establish an electric field that activates the ER fluid 520 such that the viscosity of the ER fluid 520 increases. The increased viscosity of the ER fluid 520 makes the entire sheath 516 and fiber bundle 514 much more rigid in comparison to the inactivated state when the fibers 510, 512 are not energized. The entire bundle 514 and sheath 516 extend longitudinally such that when rigid, the bundle and sheath form beams running surrounding the knee, which increases the modulus of the brace.

Figure 8:
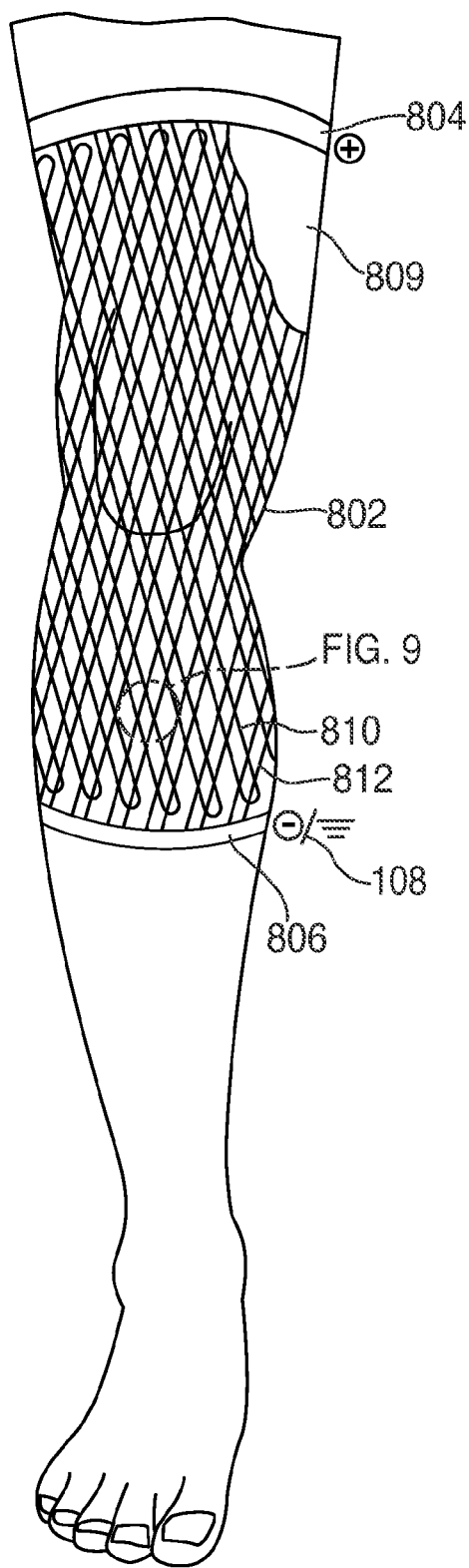
FIG. 8 is an elevation view showing another embodiment of a knee brace worn on a leg in accordance with an aspect of the application.

FIG. 8 shows another embodiment of a knee brace 802. The knee brace 802 includes opposite polarity terminals 804, 806 at opposite ends of the brace 802 spaced longitudinally apart between a looped weave of opposite polarity insulated conductive fibers 810, 812. In the looped weave, a positive conductive fiber 810 extends towards the negative terminal 806 and returns to the positive conductive terminal 804, while the negative conductive fiber 812 extends towards the positive terminal 804 and returns to the negative terminal 806. The negative fiber loop 812 is spaced from the positive terminal 804 and the positive loop 810 is spaced from the negative terminal 806. In one embodiment, the conductive fiber loops 810, 812 are interwoven, like the arrangement shown in FIG. 9.

Figure 9:
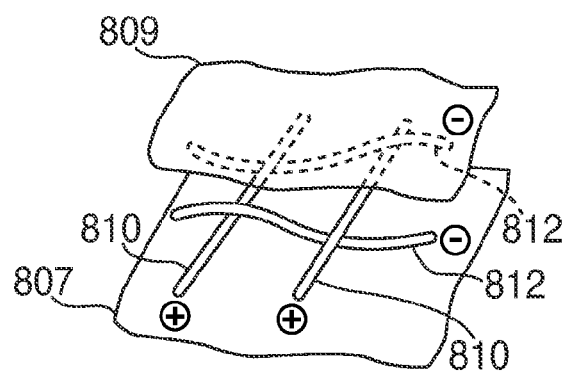
FIG. 9 shows a partial cutaway view of woven conductive fibers of the knee brace of FIG. 8.

The brace includes an inner cylindrical sheath 807 (FIG. 9) and an outer cylindrical sheath 809 (FIGS. 8 and 9) that define an annular space in which the conductive woven loops 810, 812 are disposed. In one embodiment, the annular space contains an ER fluid (not shown) in contact with the fiber loops 810, 812. The ER fluid is activated by electrifying the conductive fibers 810, 812, thereby increasing the modulus of the brace 802 in comparison to the modulus when the conductive fibers 810, 812 are not electrified and do not activate the ER fluid. The amount of crossover between the conductive fibers 810, 812 shown in FIG. 9 is intermediate between the warp/weft weave of the embodiment shown in FIGS. 1 to 4 and the twisted weave shown in FIGS. 5 to 7.

It should be appreciated that combinations of the weft/warp weave, bundle weave, and looped weave embodiments are possible. For example, in another embodiment, not shown, a looped weave of conductive fibers, such as that described above in connection with FIGS. 8 and 9 is combined with a bundle weave of twisted conductive fibers, such as those described above in connection with FIGS. 5 to 7. Such combinations of woven arrangements can increase the rigidity of any one of the individual woven arrangements. For example, the looped weave can improve the torsional rigidity of the knee brace employing only a bundled weave.

In the warp/weft, bundled, and looped weave arrangements, it may be easier to lay up the opposite polarity conductive fibers without interleaving the conductive fibers by using a non-conducting filament or thread to "quilt" the resulting layup in order to tie all of the fibers together. For example, in the warp/weft weave, the construction can include a layer of warp, followed by a layer of weft, and an interwoven quilting of non-conducting filament to bind the warp and weft together.

Figure 10:
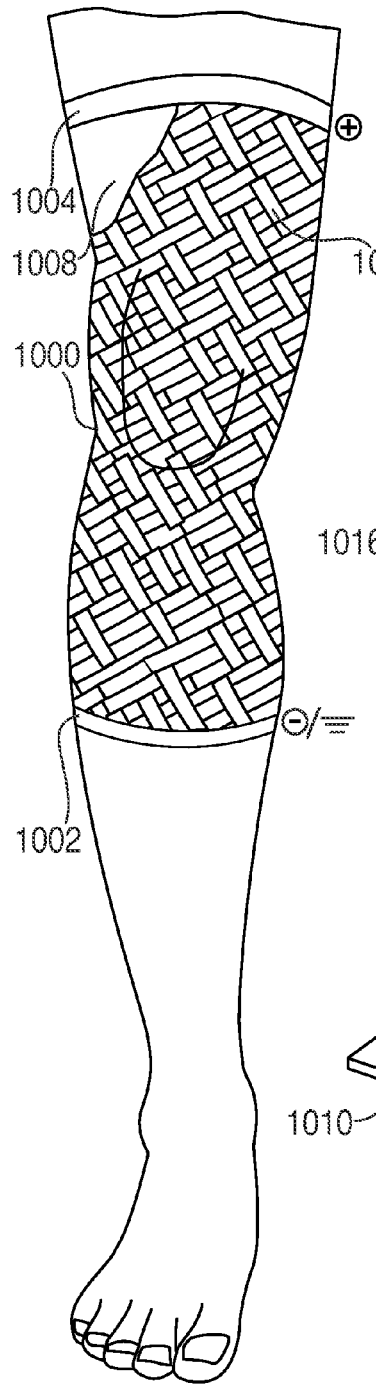
FIG. 10 is an elevation view showing another knee brace worn on a leg in accordance with an aspect of the application.
Figure 11:
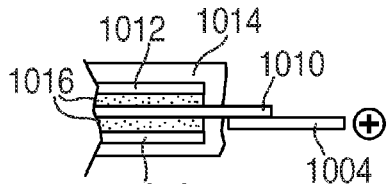
FIG. 11 is an exploded side elevation view of a portion of the knee brace shown in FIG. 10.
Figure 12:
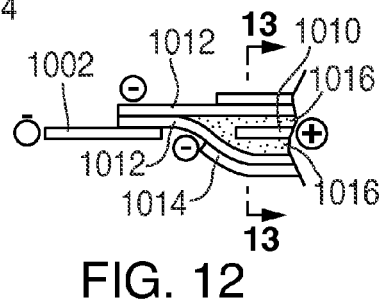
FIG. 12 is an exploded side elevation view of a portion of the knee brace shown in FIG. 10.

FIG. 10 shows yet another embodiment of a knee brace 1000 formed of oppositely spaced apart terminals 1002, 1004 connected by a basket weave of flat conductive strips 1006. The knee brace 1000 is preferably covered with a cover 1008. Each strip 1006 is a multilayered structure, including flat conductive fibers 1010, 1012 of alternating polarities. For example, in one embodiment, each strip 1006 has three conductive fibers 1012, 1010, 1012, formed as flat conductors, such as that shown in FIGS. 11 to 13, where the outer conductive fibers 1012 are negative and the inner conductive fiber 1010 is positive. As shown in FIG. 11, the inner conductive fiber 1010 is electrically connected to the positive terminal 1004 at one end of the strip 1006. As shown in FIG. 12, the outer conductive fibers 1012 are electrically connected to the negative terminal 1002 at another end of the strip 1006. The outer conductive fibers 1012 are all of the same polarity to avoid an electrical short between multiple woven strips 1006.

Figure 13:
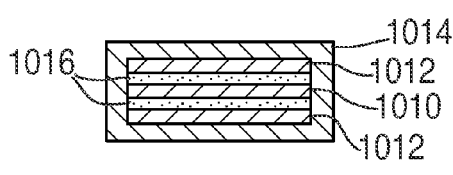
FIG. 13 is a view of the portion of the knee brace shown in FIG. 12 along section 13-13.

FIG. 13 shows a view of the strip 1006 along section 13-13 in FIG. 12. As shown in FIG. 13, the strip 1006 is enclosed in a flexible member 1014. Within the strip 1006 the opposite polarity conductive fibers 1010, 1012 are spaced apart to prevent shorting. To maintain the spacing between the fibers 1010, 1012 and provide electrical isolation, various spacing arrangements are possible.

In one embodiment an ER fluid 1016 is contained between the conductive fibers 1010, 1012. Although the ER fluid 1016 is dielectric, because it can flow, it cannot be counted on to maintain fiber-to-fiber dielectric spacing within strip 1006 and, therefore, cannot be counted to prevent shorting. Therefore auxiliary dielectric spacing arrangements can be employed to maintain dielectric spacing between the conductive fibers 1010, 1012 of the strip 1006, as described hereinbelow.

Thus, in one alternate embodiment, relatively large dielectric particles (e.g. 50-100 micron spheres, compared to the 50-100 nanometer dielectric particles typically found in ER fluid) are suspended in the ER fluid 1016. Such large dielectric particles in the ER fluid 1016 are randomly distributed and can provide mechanical and electrical separation of the fibers 1010, 1012. For example, such large dielectric particles can be formed as microglass spheres manufactured by 3M Corp., of St. Paul, Minn.

Figure 14:
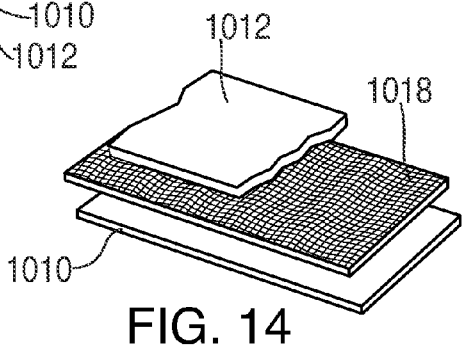
FIG. 14 is a partial assembly view of an alternative embodiment of the portions shown in FIGS. 11 to 13.

FIG. 14 shows an embodiment of a portion of the strip 1006 in which a fiber mat or woven fabric 1018 is also positioned between the conductive fibers 1010, 1012 of the strip 1006. Though not shown in FIG. 14, the ER fluid 1016 is also positioned between the conductive fibers 1010, 1012. In one embodiment, the fiber mat or woven fabric 1018 has a porosity that allows the ER fluid 1016 to freely contact adjacent conductive fibers 1010, 1012. In one embodiment, the fiber mat or woven fabric 1018 is a random mat-type fabric spacer, such as a high porosity paper. For example, the spacer can be made of Kimwipes™, available from Kimberly-Clark™ of Neenah, Wis. In another embodiment, a conductive fiber and a fiber mat/woven fabric are combined together in a single element as a woven/matt fabric that has been metalized on one side.

Figure 15:
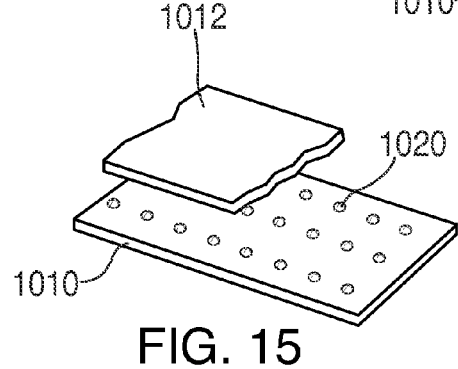
FIG. 15 is a partial assembly view of another alternative embodiment of the portions shown in FIGS. 11 to 13.

FIG. 15 shows another embodiment of the strip 1006 in which fibers 1010, 1012 are spaced apart by discrete dielectric spacers 1020, which are used in conjunction with ER fluid 1016. Though not shown in FIG. 14, the ER fluid 1016 is also positioned between the conductive fibers 1010, 1012 and around the dielectric spacers 1020. The dielectric spacers 1020 can be formed on each of the fibers 1010 and 1012 by etching continuous dielectric layers on the fibers 1010, 1012. As an alternative to etching dielectric layers, discrete deposition of dielectric spacers can be employed to form the spacers 1020. Deposition can be performed with 3-D printing methods. Both etching and deposition allow greater control over the dielectric thickness than fabric or woven spacers. Moreover, greater dimensional control of the spacing between the conductive fibers 1010, 1012 can allow closer conductive fiber spacing compared with fabric or woven spacers with the attendant benefits of lower operating voltage and lower differential shear between fibers 1010, 1012.

Figure 16:
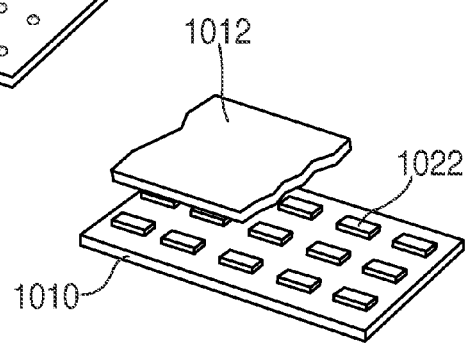
FIG. 16 is a partial assembly view of another alternative embodiment of the portions shown in FIGS. 11 to 13.

FIG. 16 shows another embodiment of the strip 1006 in which EAP 1022 strips are applied to adjacent conductive fibers 1010, 1012 as a substitute for ER fluid 1016. The EAP is a dielectric that provides electric isolation between the conductive fibers 1010, 1012. In addition to providing dielectric spacing, the EAP strips 1022 material can deform when activated, in the manner described above in connection with the description of strips 126 in FIG. 4. For example, when the EAP strips 1022 are activated, the strips 1022 on the adjacent conductive fibers 1010, 1012 link together and bind the conductive fibers 1010, 1012 together to increase the modulus of the strip 1006.

The individual strips 1006 can have a width that is 2 to 10 times the thickness of the strip 1006. For example, in one embodiment, a three layer strip with 50 micron spacing between each conductive fiber and an overall thickness of about 200-250 microns might have a width between 500 to 5000 microns (0.5 to 5 mm) wide, which provides for a relatively fine texture.

In any of the embodiments employing woven conductive fibers described above, such as warp-weft weaving, bundled interlaced conductive fibers, and fiber loop weaving, it is necessary to avoid shorting of the conductive fibers. To achieve electric isolation between the opposite polarity conductive fibers, in at least one embodiment, at least the conductive fibers of one polarity are coated or otherwise separated from fibers of opposite polarity with a dielectric spacer. Because EAP materials are also dielectric, EAP can serve both as a dielectric and a cross-linking agent between the conductive fibers, as described above. Additional conductive fiber geometries and arrangements of fibers bearing EAP are also possible, as described hereinbelow without limitation.

For example, FIG. 17 shows an embodiment of a conductive fiber 1702 on which a plurality of discrete EAP strips 1704 are attached to the outer surface of the fiber 1702. The strips 1704 extend longitudinally and are spaced circumferentially around the conductive fiber 1702. While the strips 1704 shown in FIG. 17 have a generally rectangular cross-section, in other embodiments, the cross-section can have other shapes, such as semicircular, for example. Each strip 1704 is attached at one of its ends to the conductive fiber 1702. In alternate embodiments the strips 1704 can be arranged in a circumferential or helical orientation.

In embodiments of the knee brace in which ER fluid is not used, such as with respect to the braces shown FIGS. 4 and 16, the flexure properties of the EAP material alone is used to increase the modulus of the knee brace by cross-linking EAP strips of neighboring fibers when activated. In such embodiments employing EAP, the percentage of conductive fiber surface that can be covered with the EAP strips can be very high (up to 99%), however the characteristic (circumferential) width must be small enough to not increase either the fiber stiffness in the inactivated state (by increasing the effective area moment of inertia), or impede the EAP deployment (significant curvature of the EAP in the plane defined by the fiber axis). In one embodiment, the characteristic (circumferential) width of each strip is less than 10% of the circumference (i.e., spanning an arc of less than 36 degrees for round fibers).

Figure 18:
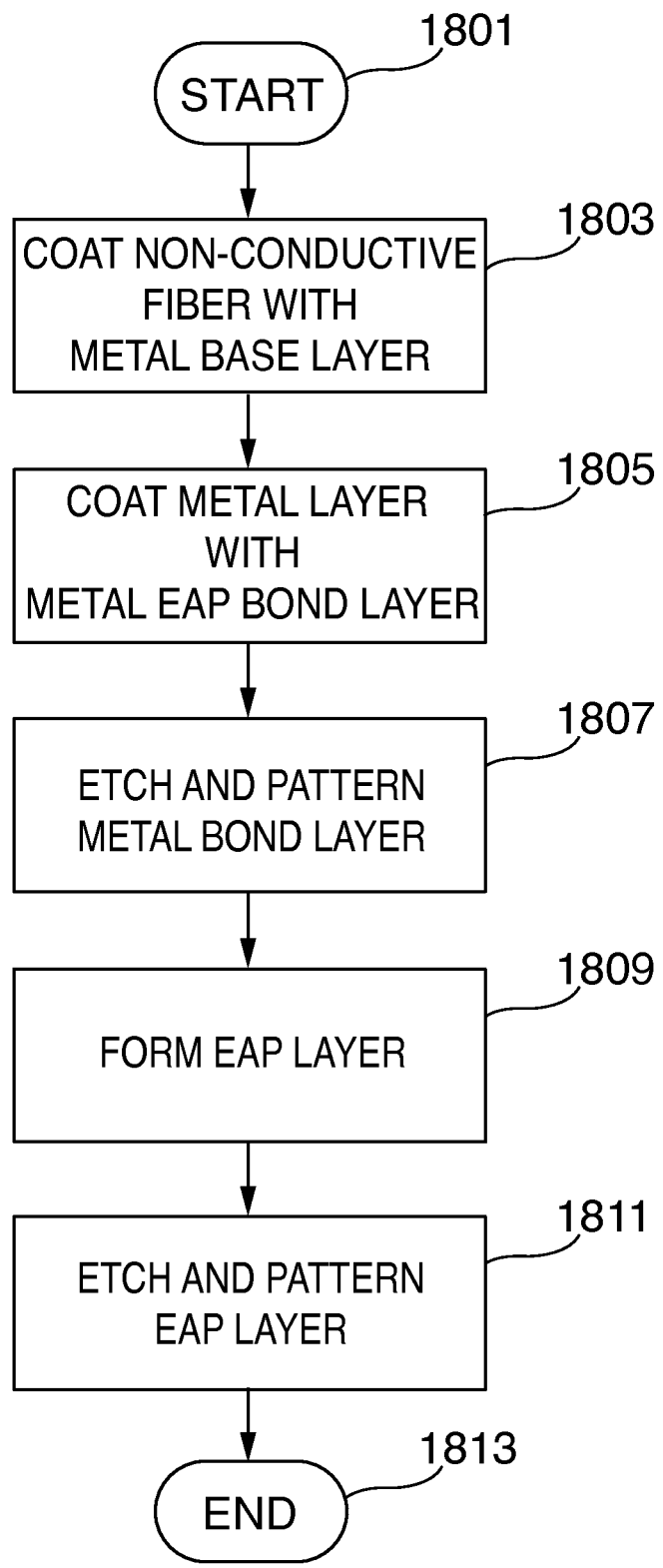
FIG. 18 is a flowchart of a process of forming a conductive fiber in accordance with an aspect of the application.

The strips 1704 can be formed on the conductive fibers 1702 by etching uniform surface layers of EAP in a multistep process. For example, one embodiment of a method of forming the conductive fiber shown in FIG. 17 is described with reference to FIG. 18. Initially, at 1801 a non-conductive polymer fiber is provided. At 1803, the non-conductive polymer fiber is coated with a metal layer to provide conductivity for the conductive fiber. At 1805, the metalized polymer is subsequently coated with a metal EAP bond layer. The metal EAP bond layer provides surfaces to which the EAP material can selectively bond in a subsequent operation. For example, such selective bonding allows one end of an EAP strip (e.g., 1022, FIG. 16; 126, FIG. 4) to be attached to the fiber while allowing an opposite end of the EAP strip to be free to deflect from the fiber in an activated state, as described above. At 1807 the metal EAP bond layer is etched and patterned to provide a geometric pattern that would allow a subsequent EAP layer to be selectively bonded. At 1809 an EAP layer is formed on the EAP bond layer. At 1811 the EAP layer is etched and patterned to create the individual EAP strips and at 1813 the conductive fiber is fully formed and the process ends.

FIG. 19 shows two of the conductive fibers 1702 shown in FIG. 17 adjacent to each other in an activated state when the EAP strips 1704 on each conductive fiber 1702 is subjected to an electric field. When activated, the unattached ends of the strips 1704 deflect radially away from respective fiber axes A and B and link together to join the adjacent conductive fibers 1702.

Owing to charge build-up in the EAP, a conduction path between the conductive fibers and the EAP is provided so that the surface charge on the dielectric EAP will migrate to the conductive portion of the fiber and not eventually negate the electric field generated by the conductive fibers. Also, in another embodiment, alternating current (AC) is used to electrify the conductive fibers to mitigate the charge build-up in the EAP. Where AC is used, the AC cycle frequency is longer than the nominal response time of the EAP (the time between an electric field being generated and the time at which the EAP deflects) and the AC wave is conditioned to be a square, pulse-shaped wave.

FIG. 20 shows another embodiment of a conductive fiber that includes a fiber 2002 and long EAP strips 2004. The EAP strips 2004 are attached everywhere along their lengths to the conductive fiber 2002. The longer length of the EAP strips 2004 and the continuous attachment along their length can distort the shape of the entire conductive fiber 2002 when the long strips 2004 are activated, as shown in FIG. 21. The distortion of the conductive fiber 2002 can be increased if the circumferential electric field applied to the strips 2004 is not uniform and/or if the long strips 2004 are asymmetrically circumferentially positioned on the conductive fiber 2002. The distortion will result in increased bulk material stiffness of a brace formed from fibers 2002 having strips 2004 by two mechanisms: 1) fiber-to-fiber physical interaction due to distortion and 2) pre-stressing the entire structure when the fiber overall length shortens to accommodate local deformations in the fiber. In one embodiment, the conductive fiber 2002 and strips 2004 can be formed by coating the conductive fiber 2002 with a layer of EAP and selectively etching the EAP layer to form the strips 2004.

For woven conductive fiber arrangements that primarily rely on the activation of ER fluid to increase the modulus of elasticity ("ER-based fiber arrangements"), EAP is applied to the conductive fibers mainly for its dielectric properties and not for its flexure properties. Therefore, for embodiments of braces in which ER fluid is used, the EAP dielectric can be applied to the conductive fibers without regard to specific EAP flexure or bonding parameters described hereinabove. However, for woven conductive fiber arrangements that rely on both ER fluid and EAP cross-linking to increase the modulus of elasticity, the EAP flexure and bonding parameters are considered so that the cross-linking effects of both ER fluid and EAP are obtained.

For example, FIG. 22 shows an embodiment of a conductive fiber 2302 that can be used in an ER-based arrangement. Fiber 2302 includes an inner metal core 2304 surrounded by a dielectric layer 2306. The dielectric layer 2306 is porous to permit ER fluid to reach the inner metal core 2304. Owing to charge transfers occurring in the ER fluid, it is advantageous to allow some ER fluid to contact the core 2304 to prevent a charge build-up that can negate the electric field in the ER fluid. In FIG. 22, discrete holes 2308 are shown. However, instead of discrete holes 2308, the dielectric can have smaller, more randomized pores that permit ER fluid to reach the core 2304. In that regard, typical particles in the ER fluid are 10 nm to 10 microns in size, so the dimensions of any holes or pores can be as small as 0.5 micron to 20 microns.

Figure 23:
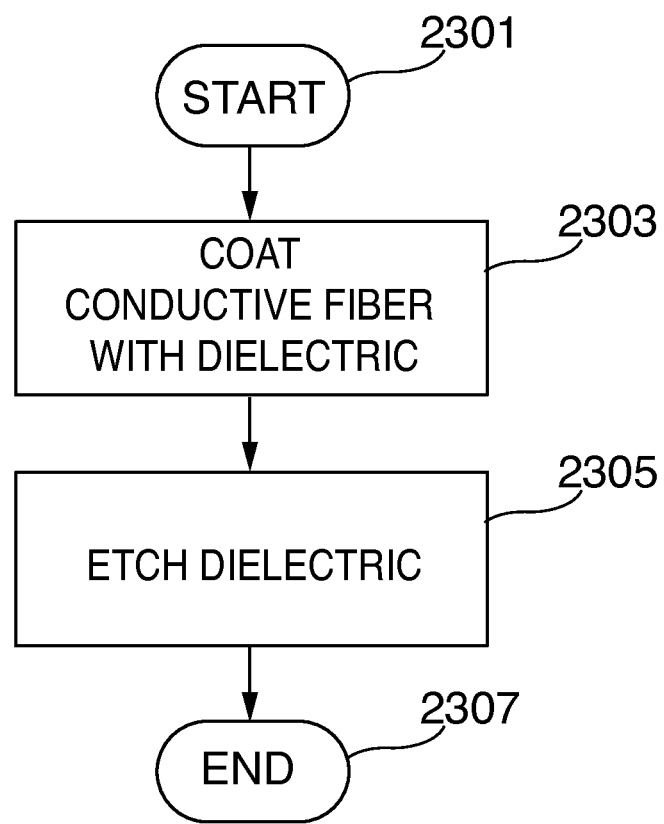
FIG. 23 is a flowchart of a process of forming a conductive fiber in accordance with an aspect of the application.

FIG. 23 is a flow chart of a process of forming the conductive fiber shown in FIG. 22. Initially, at 2301 a conductive fiber (metal thread, conductive polymer, metalized polymer) is provided. At 2303, the conductive fiber is coated with a dielectric material. At 2305 the dielectric material is etched to produce small openings to the inner conductive fiber and at 2307 the conductive fiber 2302 is fully formed and the process ends. As an alternative to etching the dielectric material in 2305, dielectric materials can be selected, which when deposited at 2303, inherently have a porosity sufficient to permit ER fluid to pass through the dielectric material to the inner conductive fiber. For example, in one embodiment, the dielectric material is PTFE that is deposited under certain conditions which inherently form micropores in the PTFE, similar to the structure of GORE-TEX®, available from W. L. Gore & Associates of Elkton, Md. In another embodiment, a dielectric material is deposited on a selectively prepared surface that wets/repels to encourage porosity in the dielectric material that is deposited. For example, in one embodiment, the dielectric material is deposited in a PVD process where surface variations in the inner conductive fiber lead to columnar hole defects in the deposited dielectric material.

FIG. 24 shows another embodiment of a conductive fiber 2402 that can be used in an ER-based arrangement. The fiber 2402 is surrounded by longitudinal dielectric strips 2404, such as EAP, which are formed by a die cutting process. For example, in one embodiment the fiber 2402 can be formed from a solid or hollow dielectric core 2406 that is coated with a metal layer. The metal layer is further coated with a dielectric layer of, for example, EAP. Such a coated core 2406 is passed through a cutting die to cut ridges in the dielectric layer that extend radially to the metal layer. The strips 2404 of dielectric material remain after the ridges are cut. In another example, instead of the core 2406 being metalized with a layer of metal, the core is formed as a solid inner metal filament that is coated with an outer dielectric material, such as EAP. Such a solid metal coated core 2406 is passed through a cutting die to cut ridges in the dielectric layer that extend to the metal filament, thereby leaving behind the strips 2404.

FIG. 25 shows another embodiment of a die-cut fiber 2502 that can be used in an ER-based arrangement. Fiber 2502 includes a core 2506 on which a helical dielectric strip 2504, which can be made of EAP, is formed in a die-cutting process, such as the process described above for fiber 2402.

FIG. 26 shows a schematic of multiple conductive fibers 2602 of opposite plurality. FIG. 27 shows an approximate quadrupole electric field produced from four of the conductive fibers in FIG. 26 (two positive fibers and two negative fibers) when the fibers 2602 are energized by a power source, such as a DC or AC source. The general shape of the quadrupole would be repeated as the number of conductive fibers is increased. Maximum field strength is between the closest opposite polarity wires. Field strength is circumferentially asymmetric.

Figure 28:
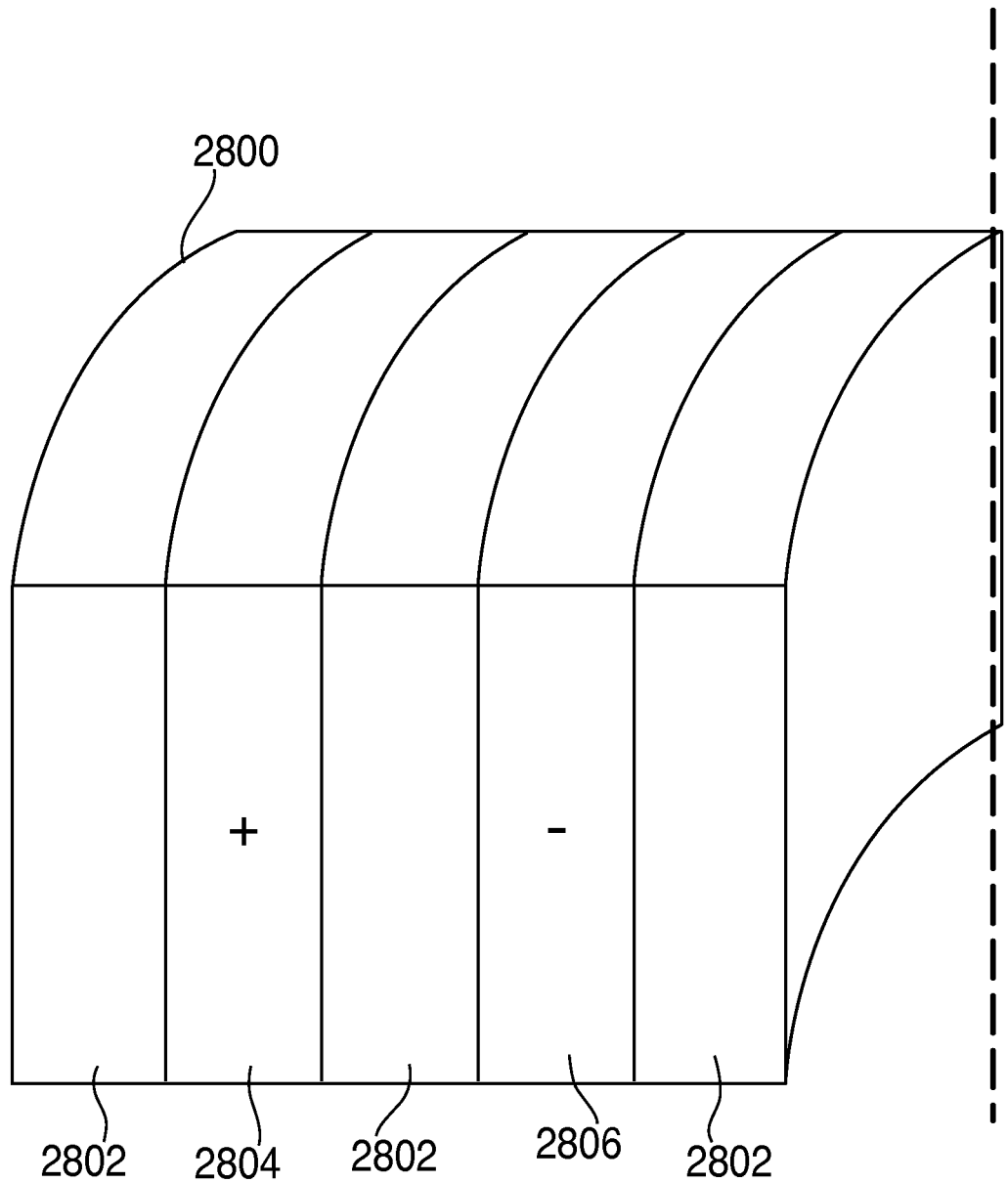
FIG. 28 shows a schematic view of another embodiment of a knee brace in accordance with an aspect of the application.

FIG. 28 shows a schematic a portion of another embodiment of a knee brace 2800. The knee brace 2800 is formed using cylindrical, dielectric fabric layers 2802 as spacers between separate cylindrical conductive fabric layers 2804, 2806. By way of example and not limitation, the dielectric fabric layers can include one of mesquito netting and panty hose nylon weave, cotton gauze, pressed fiber paper (e.g. kimwipes), electrospun fibers, spin coatings of polyvinylidene difluoride (PVDF) with water emulsions or sodium bicarbonate to form pours, commercial membrane products such as PVDF membranes, available from Sterlitech Corporation of Kent, Wash., and from Novamem LLC of Zurich, Switzerland. Also, by way of example and not limitation, the conductive fabric layers 2804, 2806 can be formed of a silver coated cotton fabric (termed "sanisilver"), a copper wire weave, and a silver coated fiber weave.

Although each conductive fabric layer 2804, 2806 and dielectric fabric layer 2802 can be separate elements, in at least one embodiment, one or more of those layers can be combined, such as where a dielectric fabric is used that has been metalized on one side, such as a silver side of a sanisilver cotton fabric. In one embodiment, the fabric layers 2802 are constructed to contain an ER fluid in contact with the conductive fabric layers 2804, 2806. If the fabric layers 2802 are porous to the ER fluid, a non-porous membrane can also be used in conjunction with, or in place of, the fabric layers 2802 to contain the ER fluid in contact with the conductors of the respective polarity conductive fabric layers 2804, 2806. Also, in at least one embodiment, the ER fluid can be contained in matrices of the conductive fabric 2804, 2806 by surface tension.

In another embodiment, each conductive fabric layers 2804 and 2806 can be formed as a weave of insulated conductive fibers like those weaves shown in FIGS. 1, 5, and 8. However, instead of weaving conductors of opposite polarity together, all of the woven fibers of each layer 2804 and 2806 will be of the same polarity.

FIG. 29 shows an embodiment of a knee brace system 2900. The system includes a knee brace 2902, a power source 2904, a switch 2906, and at least one sensor 2908 connected to the knee brace 2902. The knee brace 2902 can be any of the knee braces described above.

FIG. 30 shows a wiring diagram of the knee brace system 2900 of FIG. 29. The power source is connected in parallel with (1) the sensor 2908 and (2) the knee brace 2902 and the switch 2906. Thus, the sensor 2908 is powered regardless of the state of the switch 2906. The sensor 2908 is constructed to sense a condition that triggers a change of state of the switch 2906. The switch 2906 is constructed to change state based on the condition sensed by the sensor 2908. When the switch 2906 is in a first "off" position, no power is applied to the conductive fibers of the knee brace 2902, such that the knee brace 2902 remains compliant and flexible. When the switch is in a second "on" position, power is applied to the conductive fibers of the knee brace 2902 to activate the ER/EAP such that the knee brace 2902 becomes rigid, as described above.

In one embodiment, the sensor 2908 can include one or more accelerometers placed on the knee brace 2902. In one embodiment, accelerometers are placed at three locations on the knee brace 2902, suitably to provide measurements to compute a valgus angle deformation. Of course, other sensors that are spaced from the brace and which are located at other parts of the wearer's body can be employed in conjunction with one or more sensors on the brace. For example, in one embodiment, one sensor can also be placed on a helmet or head covering worn by the wearer of the brace. The acceleration measurements can be integrated using conventional algorithms executed by a processor (not shown) integrated with the sensor 2908 to determine the position of the knee and portions of the leg to compute the valgus angle deflection. Also, at least one sensor, such as a strain sensor, can be positioned on the part of the wearer to be protected to directly measure muscle and ligament strain rather than indirectly through acceleration measurements and computation of the valgus deflection angle. Since integration only needs to occur on time scales of several milliseconds, extremely precise accelerometers are not needed. For example, in one embodiment, MEMS-type accelerometers can be used. The sensors 2908 can also include a comparison algorithm to continuously compare the valgus angle to a threshold valgus angle at which point activation of the knee brace will be triggered by closing the switch 2906 to energize the conductive fibers of the brace 2902.

It will be appreciated that similar accelerometer arrangements can be employed for a neck brace constructed in the same manner as the knee brace. Acceleration is the established means to measure and predict concussion injury. Accelerometers with a basic threshold comparison algorithm would be sufficient to trigger and activate the neck brace. For example, continuous monitoring of the valgus angle using the accelerometers can be used to trigger activation of the neck brace once the valgus angle is at least a predetermined angle, such as 4 degrees.

In one embodiment, the sensor 2908 is constructed to sense impact forces on the knee brace from at least one strain gauge on the knee brace. The sensor 2908 is constructed to transmit a signal to the switch 2906 based on the sensed force. The switch 2906 can be constructed as a MOFSET-type switch that only energize the brace 2902 when the sensed strain is equal to or exceeds a predetermined strain corresponding to a maximum strain, termed an activation strain. For example, as shown in the graph of FIG. 31, during the period between time $t_0$ and $t_{activate}$ the strain measured is less than the activation strain, during which period the knee brace 2902 is not activated and is flexible. However, at $t_{activate}$ the strain is equal to the activation strain and therefore the knee brace 2902 becomes active and is rigid.

In one embodiment, the knee brace 2902 is powered by several hundred volts from either a capacitor or a DC boost circuit using solid state switching. Capacitances on the order of several μF would be expected, and leakage currents about 10 mA (total power of 10 W for a 1000V supply). In most cases the injury event would be over in a second, so total energy requirements would be 1-10 Joules, which, in comparison, is far less than the 5000 Joule output of one AAA alkaline battery.

As noted above, typical sports injuries typically occur during a relatively short time period. For example, ACL and MCL injuries to the knee can occur in a period of about 15 milliseconds. In order to aid in protecting the wearer during such intervals, the total of the reaction time of system 2900 to activate the brace 2902 and the activation time of the ER fluid and/or EAP in the brace 2902 is preferably less than the duration in which injury can occur. Also, the total of the reaction time of system 2900 to deactivate the brace 2902 and the deactivation time of the ER fluid and/or EAP in the brace 2902 is preferably less than the duration in which injury can occur in order to allow the wearer to resume flexibility of the brace as quickly as possible after deactivation.

The foregoing embodiments of a brace have been described in the context of a knee brace. The knee brace shown in the embodiments can help protect from injuries to the medial collateral ligament (MCL), which is a popular sports injury. In use, the knee braces described above can facilitate the transfer of an impulse function and/or peak force of impact to the knee to another location so as to limit or prevent injury of the MCL.

A knee brace that is stiff enough can either distribute the load along the knee brace or move it to the ends of the brace. The stiffer the knee brace is, the more the maximum stress on the MCL can be reduced. The stiffness depends on the geometry and the modulus of the brace. The annular geometry of the knee braces described hereinabove provides a moment of inertia that is preferable to that of conventional knee braces. Moreover, the variable elastic modulus of the knee brace from a compliant "knee sock" when inactive to a stiff cylinder when active further utilizes this favorable geometry to selectively increase the rigidity of the brace in response to changes in force applied to the knee.

As discussed above, the embodiments of the knee brace described above can be modified in dimension and/or shape for use as a neck brace. The detrimental forces that can injure an athlete develop from head acceleration rather than impact forces directly. A neck brace constructed as described above can be used to stiffen around the neck and link the head to the torso to reduce maximum acceleration experienced by the head.

In addition, in one embodiment, a larger neck brace covering the shoulders, neck and at least part of the head allows unrestricted head movement in the inactivated state. For example, an upper portion of such a brace can be formed to resemble a balaclava, covering the neck and head, while a lower portion can extend to cover the chest and upper arms and shoulders; the overall brace reminiscent of medieval armor worn by knights. When activated, the brace links the head and shoulders so that forces applied directly to the head are partially transmitted to the upper torso, reducing acceleration (and deflection) of the head. A direct body blow that moves the body away from the head and then snaps the head back would be mitigated as the head would again get linked to the heavier upper torso, slowing its acceleration.

In yet another embodiment, one or another of the neck braces described above are used in conjunction with a helmet and a helmet-mounted sensor. The helmet preferably has an outer surface that is slippery so that when forceful contact is made between two helmets, such as during a football scrimmage, a deflection will occur reducing the effects of the impact on both players. For example, the helmet can be coated at least partially with Teflon® or similar slippery material. Also, the helmet-mounted sensor is configured to sense the severity of head impacts sustained by the wearer and can be connected to the neck brace to act as the trigger to activate and stiffen the neck brace in the event of a head impact above a predetermined severity that is detected by the sensor. An example of such a sensor is the Reebok CHECKLIGHT, manufactured by Reebok International (http://shop.reebok.com/us/content/CheckLight; last viewed on Mar. 28, 2014).

By using a material that is ordinarily compliant when not activated, and which can stiffen when activated, it is possible to surround portions of the body with a brace material that will be comfortable enough to the wearer and achieves a higher level of stress reduction compared to a conventional brace, such that wearers of the brace will be encouraged to wear the brace prophylactically.

There have been described and illustrated herein several embodiments of a brace and a method of making conductive fibers for a brace. While particular embodiments have been described, it is not intended that the invention be limited thereto, as it is intended that the invention be as broad in scope as the art will allow and that the specification be read likewise. Thus, while particular apparatus, system, and methods have been disclosed, it will be appreciated that other equivalents of those are included as well. In addition, while particular types of materials for components of the braces have been disclosed, it will be understood that other equivalent materials can be used. Moreover, while particular configurations have been disclosed in reference to ER fluid and EAP fibers, it will be appreciated that other configurations could be used as well in which ER fluid and EAP fibers are used together. It will therefore be appreciated by those skilled in the art that yet other modifications could be made to the invention without deviating from its spirit and scope as claimed.

What is claimed is:

1. A brace for at least a part of a body comprising:
    a first conductive fiber associated with a first polarity; and
    a second conductive fiber associated with a second polarity different from the first polarity, the second fiber woven together with the first fiber and insulated from the first fiber; and
    a selectively electrically activated cross-linking agent between the first and second fiber, wherein the agent is constructed to limit relative movement of the first and second fibers in a first active mode when the first and second fibers are electrified.

2. The brace according to claim 1, further comprising a first terminal electrically connected to the first conductive fiber and a second terminal electrically connected to the second conductive fibers, wherein the first and second terminals are electrically isolated from each other.

3. The brace according to claim 2, wherein at least one of the first conductive fiber and the second conductive fiber includes electrical insulation.

4. The brace according to claim 3, wherein the first plurality of fibers and the second plurality of fibers are arranged in a warp/weft pattern in which the first fiber forms the warp and the second fiber forms the weft.

5. The brace according to claim 4, wherein the cross-linking agent includes an ER fluid retained in contact with the first fiber and the second fiber.

6. The brace according to claim 4, wherein the cross-linking agent includes an EAP dielectric attached to the first fiber and the second fiber.

7. The brace according to claim 3, wherein the first terminal and the second terminal are spaced longitudinally from each other and wherein the first conductive fiber extends longitudinally from the first terminal towards the second terminal, but is spaced therefrom and the second conductive fiber extends longitudinally from the second terminal towards the first terminal but is spaced therefrom, and wherein the first conductive fiber is intertwined with the second conductive fiber longitudinally.

8. The brace according to claim 7, further including a sheath surrounding the intertwined first and second conductive fibers, wherein the agent includes an ER fluid contained by the sheath and retained in contact with the first and second conductive fibers.

9. The brace according to claim 3, wherein the first conductive fiber is formed as a first loop and has a first end and a second end attached to the first terminal and the second conductive fiber is formed as a second loop and has a first end and a second end attached to the second terminal, and wherein the first loop is woven with the second loop.

10. The brace according to claim 3, wherein the fibers have EAP strips longitudinally positioned on an outer surface of the fibers.

11. The brace according to claim 3, wherein EAP strips are circumferentially spaced and attached to the fibers at only one end of the EAP strips.

* * * * *